(12) United States Patent
Rioux et al.

(10) Patent No.: US 7,959,549 B2
(45) Date of Patent: *Jun. 14, 2011

(54) PERCUTANEOUS ARRAY DELIVERY SYSTEM

(75) Inventors: Robert F. Rioux, Ashland, MA (US); Jeffrey Bean, Fitchburg, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/721,450

(22) Filed: Mar. 10, 2010

(65) Prior Publication Data

US 2010/0168500 A1      Jul. 1, 2010

Related U.S. Application Data

(63) Continuation of application No. 12/198,818, filed on Aug. 26, 2008, now Pat. No. 7,695,424, which is a continuation of application No. 11/075,172, filed on Mar. 7, 2005, now Pat. No. 7,431,687.

(51) Int. Cl.
*A61M 37/00* (2006.01)
(52) U.S. Cl. ............................................ 600/3; 604/264
(58) Field of Classification Search .................. 600/1–8, 600/439; 604/19, 164.01–164.09, 165.01, 604/173, 264
See application file for complete search history.

(56) References Cited

U.S. PATENT DOCUMENTS

| | | | |
|---|---|---|---|
| 3,174,851 A | 3/1965 | Buehler et al. | |
| 3,351,463 A | 11/1967 | Rozner et al. | |
| 3,753,700 A | 8/1973 | Harrison et al. | |
| 5,419,777 A | 5/1995 | Hofling | |
| 5,855,576 A | 1/1999 | LeVeen et al. | |
| 6,796,935 B1 | 9/2004 | Savino | |
| 7,431,687 B2 | 10/2008 | Rioux et al. | |
| 7,695,424 B2 * | 4/2010 | Rioux et al. | 600/3 |
| 2004/0116920 A1 | 6/2004 | Rioux et al. | |

FOREIGN PATENT DOCUMENTS

| | | |
|---|---|---|
| EP | 1 402 922 | 3/2004 |
| WO | WO 00/40281 | 7/2000 |
| WO | WO 02/00278 | 1/2002 |

OTHER PUBLICATIONS

PCT International Search Report for PCT/US2006/007491, Applicant Boston Scientific Scimed, Inc., Form PCT/ISA/210 and 220, dated Jul. 3, 2006 (5 pages).
PCT Written Opinion of the International Search Authority for PCT/US2006/007491, Applicant Boston Scientific Scimed, Inc., Form PCT/ISA/237, dated Jul. 3, 2006 (5 pages).
International Preliminary Report on Patentability (Chapter I of the Patent Cooperation Treaty) dated Sep. 20, 2007 for related international application No. PCT/US2006/007491, Applicant: Boston Scientific Scimed, Inc. (7 pages).

* cited by examiner

*Primary Examiner* — John P Lacyk
(74) *Attorney, Agent, or Firm* — Vista IP Law Group LLP

(57) ABSTRACT

A system for treating tissue includes a cannula having a proximal end, a distal end, and a lumen extending between the proximal and the distal ends, and an array of delivery tubes at least partially disposed within the lumen, each of the delivery tube having a lumen, wherein each of the delivery tubes is slidable relative to the cannula, and has a first configuration when inside the lumen, and a second configuration when outside the lumen. A system for treating tissue includes a treatment device having a distal end, and an indexing device for controlling a longitudinal position of the distal end of the treatment device relative to a target tissue region, the indexing device having a tubular portion for receiving the treatment device.

36 Claims, 5 Drawing Sheets

PERCUTANEOUS ARRAY DELIVERY SYSTEM

RELATED APPLICATIONS

This application is a continuation of U.S. patent application Ser. No. 12/198,818, filed on Aug. 26, 2008, now issued as U.S. Pat. No. 7,695,424, which itself is a continuation of U.S. patent application Ser. No. 11/075,172, filed Mar. 7, 2005, now issued at U.S. Pat. No. 7,431,687, the entire disclosures of which are expressly incorporated by reference herein.

FIELD OF THE INVENTION

The field of the invention relates generally to systems and methods for the treatment of tissue, and more particularly, to systems and methods for performing microsphere radiotherapy.

BACKGROUND

Many types of medical procedures involve delivering treatment particles within a body. For example, physicians have injected radioactive particles into a human body for providing radioactive treatment at target tissue regions.

Currently, delivery of radioactive particles involve injecting the radioactive particles into an artery, and allowing the particles to be carried by blood stream to target site (e.g., a tumor). At the target site, the distribution of the radioactive particles depends on the geometry and configuration of the vessels at the tumor. Since vessels at a tumor site are usually irregular in pattern, the distribution of the radioactive particles at the tumor site is usually non-uniform. As a result, parts of a tumor may receive more radiation dose than desired, while other parts of the tumor may receive an insufficient amount of radiation dose, or in some case, may not receive any radiation dose.

Another problem associated with the current technique of delivering radioactive particles is that after the particles are injected into the artery, the particles may migrate to an unintended site, e.g., a healthy tissue region. As a result, the target site does not receive the intended dose of radiation, and healthy tissue at the healthy tissue region are injured by the radiation emitted by the radioactive particles.

Thus, there remains a need to provide for improved systems and methods for delivering treatment particles.

SUMMARY

In accordance with some embodiments, a system for treating tissue includes a cannula having a proximal end, a distal end, and a lumen extending between the proximal and the distal ends, and an array of delivery tubes at least partially disposed within the lumen, each of the delivery tube having a lumen, wherein each of the delivery tubes is slidable relative to the cannula, and has a first configuration when inside the lumen, and a second configuration when outside the lumen.

In accordance with other embodiments, a method for treating tissue includes inserting a cannula into a body, deploying a plurality of delivery tubes from a lumen of the cannula such that the plurality of delivery tubes are at a first position within a target tissue region, and delivering a first treatment particle from each of the plurality of delivery tubes to the target tissue region.

In accordance with other embodiments, a system for treating tissue includes a treatment device having a distal end, and an indexing device for controlling a longitudinal position of the distal end of the treatment device relative to a target tissue region, the indexing device having a tubular portion for receiving the treatment device.

Other and further aspects and features of the embodiments will be evident from reading the following detailed description of the preferred embodiments, which are intended to illustrate, not limit, the invention.

BRIEF DESCRIPTION OF THE DRAWINGS

The drawings illustrate the design and utility of preferred embodiments. It should be noted that the figures are not drawn to scale and that elements of similar structures or functions are represented by like reference numerals throughout the figures. In order to better appreciate how the above-recited and other advantages and objects of the embodiments are obtained, a more particular description of the embodiments will be rendered, which are illustrated in the accompanying drawings. Understanding that these drawings depict only typical embodiments and are not therefore to be considered limiting of its scope, the embodiments will be described and explained with additional specificity and detail through the use of the accompanying drawings in which.

DETAILED DESCRIPTION OF THE EMBODIMENTS

Figure 1:
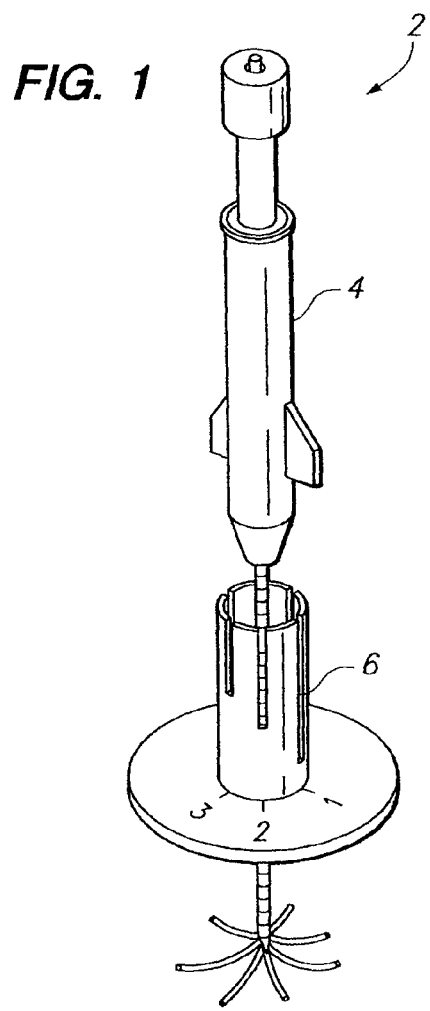
FIG. 1 is a perspective view of a tissue treatment system in accordance with some embodiments of the invention.

Various embodiments of the present invention are described hereinafter with reference to the figures. It should be noted that the figures are not drawn to scale and elements of similar structures or functions are represented by like reference numerals throughout the figures. It should also be noted that the figures are only intended to facilitate the description of specific embodiments. They are not intended as an exhaustive description of the invention or as a limitation on the scope of the invention. In addition, an aspect described in conjunction with a particular embodiment is not necessarily limited to that embodiment and can be practiced in any other embodiments.

FIG. 1 illustrates a tissue treatment system 2 in accordance with some embodiments. The tissue treatment system 2 includes a treatment device 4 configured for delivering treatment particles to a target tissue region within a body, and an indexing device 6 for controlling a position of the treatment device 4 relative to the target tissue region.

Figure 2:
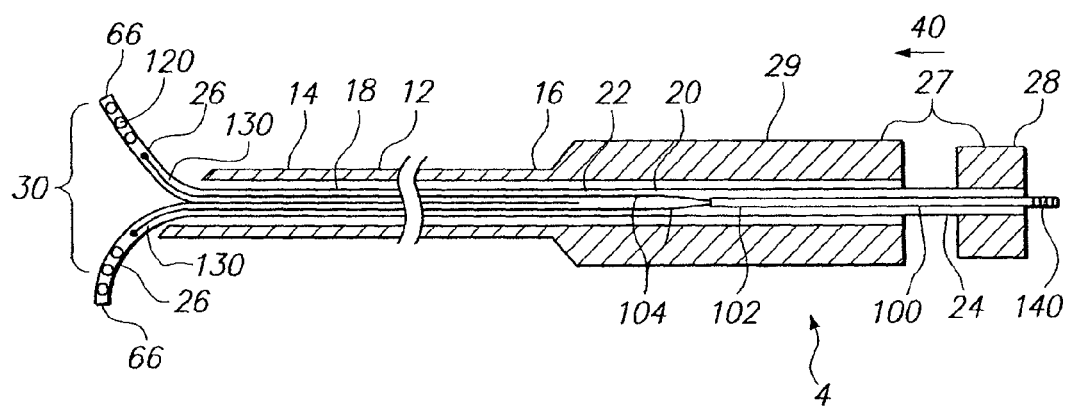
FIG. 2 is a side cross-sectional view of a treatment device used in the system of FIG. 1, wherein an array of delivery tubes is particularly shown deployed.
Figure 3:
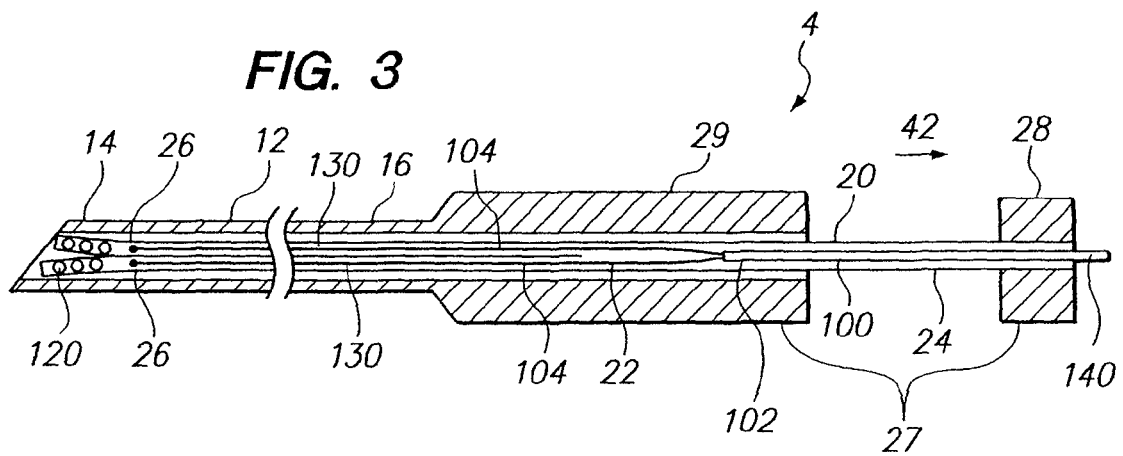
FIG. 3 is a side cross-sectional view of a treatment device used in the system of FIG. 1, wherein an array of delivery tubes is particularly shown retracted.

Referring specifically now to FIGS. 2 and 3, the treatment device 4 includes an elongate cannula 12, a shaft 20 slidably disposed within the cannula 12, and a plurality of delivery tubes 26 carried by the shaft 20. The cannula 12 has a distal end 14, a proximal end 16, and a central lumen 18 extending through the cannula 12 between the distal end 14 and the proximal end 16. The cannula 12 may be rigid, semi-rigid, or flexible depending upon the designed means for introducing the cannula 12 to the target tissue. The cannula 12 is composed of a suitable material, such as plastic, metal or the like, and has a suitable length, typically in the range from 5 cm to 30 cm, preferably from 10 cm to 20 cm. The length of the cannula 12 can also have other dimensions. The cannula 12 has an outside cross sectional dimension consistent with its intended use, typically being from 0.5 mm to 5 mm, usually from 1.3 mm to 4 mm. The cannula 12 may have an inner cross sectional dimension in the range from 0.3 mm to 4 mm, preferably from 1 mm to 3.5 mm. The cannula 12 can also have other outside and inner cross sectional dimensions in other embodiments.

It can be appreciated that longitudinal translation of the shaft 20 relative to the cannula 12 in a distal direction 40 deploys the delivery tubes 26 from the distal end 14 of the cannula 12 (FIG. 2), and longitudinal translation of the shaft 20 relative to the cannula 12 in a proximal direction 42 retracts the shaft 20 and the delivery tubes 26 into the distal end 14 of the cannula 12 (FIG. 3). The shaft 20 comprises a distal end 22 and a proximal end 24. Like the cannula 12, the shaft 20 is composed of a suitable material, such as plastic, metal or the like.

In the illustrated embodiment, each delivery tube 26 is in the form of a small diameter element, which can penetrate into tissue as it is advanced from a target site within the target region. In some embodiments, distal ends 66 of the delivery tubes 26 may be honed or sharpened to facilitate their ability to penetrate tissue. The distal ends 66 of these delivery tubes 26 may be hardened using conventional heat treatment or other metallurgical processes. In the illustrated embodiments, the delivery tubes 26 extend through the length of the cannula 12. Alternatively, the delivery tubes 26 can be shorter. For example, the delivery tubes 26 can extend through a portion of the cannula 12.

The delivery tubes 26 can have a variety of cross-sectional shapes. In the illustrated embodiments, the delivery tubes 26 have rectangular cross-sections. The rectangular cross-sections make the delivery tubes 26 stiffer in one direction (e.g., the transverse direction) and more flexible in another direction (e.g., the radial direction). By increasing transverse stiffness, proper circumferential alignment of the delivery tubes 26 within the lumen 18 of the cannula 12 is enhanced. Exemplary delivery tubes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm. In other embodiments, the cross-sections of the delivery tubes 26 may be non-rectangular. For examples, the delivery tubes 26 can have a circular, elliptical, or a square profile, and the like.

When deployed from the cannula 12, the array 30 of delivery tubes 26 has a deployed configuration that defines a volume having a periphery with a radius in the range from 0.1 to 4 cm. However, in other embodiments, the maximum radius can be other values, depending on a size and/or a geometry of a target tissue region. The delivery tubes 26 are resilient and pre-shaped to assume a desired configuration when advanced into tissue. In the illustrated embodiment, the delivery tubes 26 diverge radially outwardly from the cannula 12 in a uniform pattern, i.e., with the spacing between adjacent delivery tubes 26 diverging in a substantially uniform and/or symmetric pattern. As shown in the figure, the deployed delivery tubes 26 each has a profile that resembles at least a portion of a parabola. However, in other embodiments, each of the deployed delivery tubes 26 can have other deployed profiles, such a bent profile, a rectilinear profile, or a customized profile.

It should be noted that although a total of two delivery tubes 26 are illustrated in FIG. 2, in other embodiments, the treatment device 4 can have more or fewer than two delivery tubes 26. In exemplary embodiments, pairs of adjacent delivery tubes 26 can be spaced from each other in similar or identical, repeated patterns and can be symmetrically positioned about an axis of the shaft 20. It will be appreciated that a wide variety of particular patterns can be provided to uniformly cover the region to be treated. In other embodiments, the delivery tubes 26 may be spaced from each other in a non-uniform pattern. Such feature may be desirable to treat tissue region having a non-symmetrical geometry.

The delivery tubes 26 can be made from a variety of elastic materials. Very desirable materials of construction, from a mechanical point of view, are materials which maintain their shape despite being subjected to high stress. Certain "superelastic alloys" include nickel/titanium alloys, copper/zinc alloys, or nickel/aluminum alloys. Alloys that may be used are also described in U.S. Pat. Nos. 3,174,851, 3,351,463, and 3,753,700, the disclosures of which are hereby expressly incorporated by reference. The delivery tubes 26 may also be made from any of a wide variety of stainless steels. The delivery tubes 26 may also include the Platinum Group metals, especially platinum, rhodium, palladium, rhenium, as well as tungsten, gold, silver, tantalum, and alloys of these metals. These metals are largely biologically inert. They also have significant radiopacity to allow the delivery tubes 26 to be visualized in-situ, and their alloys may be tailored to accomplish an appropriate blend of flexibility and stiffness. They may be coated onto the delivery tubes 26 or be mixed with another material used for construction of the delivery tubes 26.

Returning to FIGS. 2 and 3, the treatment device 4 further includes a handle assembly 27, which includes a handle portion 28 mounted to the proximal end 24 of the shaft 20, and a handle body 29 mounted to the proximal end 16 of the cannula 12. The handle portion 28 is slidably engaged with the handle body 29 (and the cannula 20). The handle portion 28 and the handle body 29 can be composed of any suitable rigid material, such as, e.g., metal, plastic, or the like.

Optionally, a marker (not shown) may be placed on the handle portion 28 and/or on the proximal end 24 of the shaft 20 for indicating a rotational orientation or a position of the handle portion 28 relative to the shaft 20 (and the delivery tubes 26) during use. In some embodiments, the handle assembly 27 can have an indexing feature. For example, the proximal end 24 of the shaft 20 or the handle portion 28 can have one or more keys that mate with respective slot(s) at the interior surface of the cannula 12 or the handle body 29. Such indexing feature allows circumferential alignment of the shaft 20 (and the array 30) relative to the cannula 12. Angle indexing devices that may be used include those described in U.S. patent application Ser. No. 10/317,796, entitled "Angle Indexer For Medical Devices", the entire disclosure of which is expressly incorporated by reference herein. In other embodiments, the handle portion 28 may also include a locking mechanism (not shown) to temporarily lock against the shaft 20 to provide a more stable indexing. For example, the locking mechanism may include an axially-sliding clutch assembly that is slidable along an axis of the shaft 20 to thereby secure the handle portion 28 against the shaft 20. Other securing devices known in the art may also be used.

As shown in FIGS. 2 and 3, the treatment device 4 further includes a plunger assembly 100 for pushing treatment particles out of the lumens of the delivery tubes 26. In the illustrated embodiments, the plunger assembly 100 has a proximal portion 102, and a plurality of distal portions 104 secured to the proximal portion 102. Each of the distal portions 104 is sized to fit within a respective lumen 130 of the delivery tube 26 of the treatment device 4. Such configuration allows a plurality of treatment particles to be delivered simultaneously from the delivery tubes 26 by translating the proximal portion 102 relative to the shaft 20. In other embodiments, instead of having a common proximal end, the plunger assembly 100 can include a plurality of plungers, each of which sized to fit within a respective lumen 130 of the delivery tube 26. Such configuration allows a physician to select which of the delivery tubes 26 to use for delivering treatment particle(s) to a target site. The plunger 100 can be made from an elastic material, such as those suitable for construction of the delivery tubes 26. As shown in FIGS. 2 and 3, the plunger assembly 100 further includes markers 140 for indicating how many rounds of treatment particles 120 have been delivered (or how many rounds of treatment particles 120 remain in the treatment device 4).

In some embodiments, the delivery tubes 26 can be preloaded with the treatment particles 120. In such cases, the treatment device 4 will further include the treatment particles 120. In the illustrated embodiments, the treatment particles are radioactive. For examples, the treatment particles 120 can be coated with a radioactive substance, or be entirely made from a radioactive substance. Alternatively, the treatment particles 120 can include a bioactive agent. Also, in other embodiments, the treatment particles 120 can include an agent for harming or destroying tissue. In further embodiments, instead of solid particles, the treatment device 4 can be preloaded with liquid or a gel. For examples, the liquid or the gel can include a radioactive substance, a bioactive agent, or an agent for harming tissue.

Having described the treatment device 4, the indexing device 6 of the tissue treatment system 2 will now be described.

Figure 4:
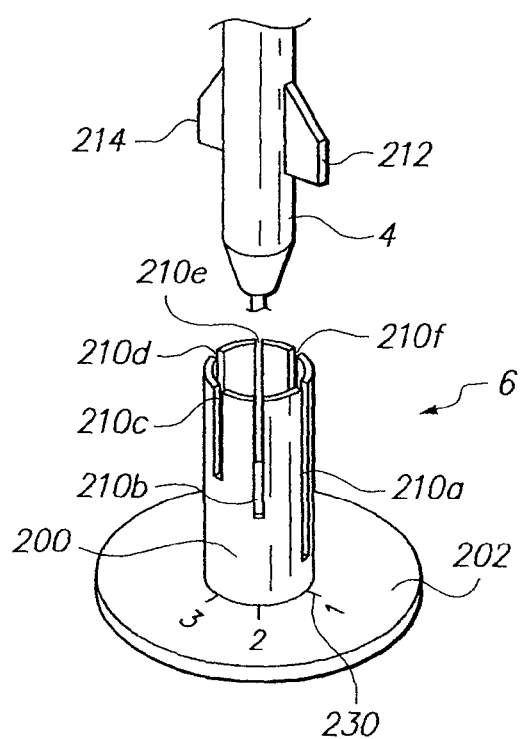
FIG. 4 is a perspective view of an indexing device used in the system of FIG. 1.

FIG. 4 shows the indexing device 6 in accordance with some embodiments. The indexing device 6 includes a tubular portion 200 sized to receive at least a portion of the treatment device 4, and a base portion 202 secured to the tubular portion 200. The base portion 202 is in a form of a disk, and is adapted to be placed on a patient's skin during use. However, in other embodiments, the base portion 202 can have other shapes and configurations. Also, in further embodiments, the indexing device 6 does not include the base portion 202. In such cases, the tubular portion 200 can be directly placed on a patient's skin during use. Although the tubular portion 200 is shown to have a circular cross section, in other embodiments, the tubular portion 200 can have other cross-sectional shapes.

In the illustrated embodiments, the indexing device 6 includes six slots 210a-210f in the wall of the tubular portion 200. The slots 210a-210c have different lengths. However, each set of opposing slots 210 have the same length. As such, slots 210a and 210d have equal lengths, slots 210b and 210e have equal lengths, and slots 210c and 210f have equal lengths. Each set of opposing slots 210 is sized to accommodate or to mate with extensions 212, 214 secured to the treatment device 4. During use, the treatment device 4 is placed into the tubular portion 200 such that the extensions 212, 214 mate with one set of opposing slots 210. The lengths of the slots 210 determine how far the treatment device 4 can translate relative to the tubular portion 200, thereby ensuring that the treatment device 4 will be positioned relative to a target tissue region in a predictable and repeatable manner. If desired, during treatment, the treatment device 4 can be retracted proximally relative to the tubular portion 200, and reinserted into the tubular portion 200 such that the extensions 212, 214 mate with another set of opposing slots 210, thereby placing the treatment device 4 at a second desired position relative to a target tissue region. As shown in FIG. 4, the base portion 202 includes markers 230 for indicating which set of slots 210 is being used. In some embodiments, the markers 230 can also include dimensions for indicating a position of a portion of the treatment device 4 relative to a reference point, such as the base portion 202, or a patient's surface. Also, in other embodiments, instead of placing the markers 230 on the base portion 202, the markers 230 can be placed on the tubular portion 200.

In other embodiments, instead of having opposing slots of equal lengths, each of the slots 210 on the indexing device 6 can have different lengths. In such cases, the treatment device 4 has one extension (e.g., extension 212) sized to alternately mate with each of the slots 210. In addition, although six slots 210a-210f are shown, in other embodiments, the indexing device 6 can have other numbers of slots. For example, the indexing device 6 can have only one slot configured to mate with an extension on the treatment device 4. Such configuration ensures that the treatment device 4 will be accurately positioned at one desired location within a target tissue region.

Figure 5:
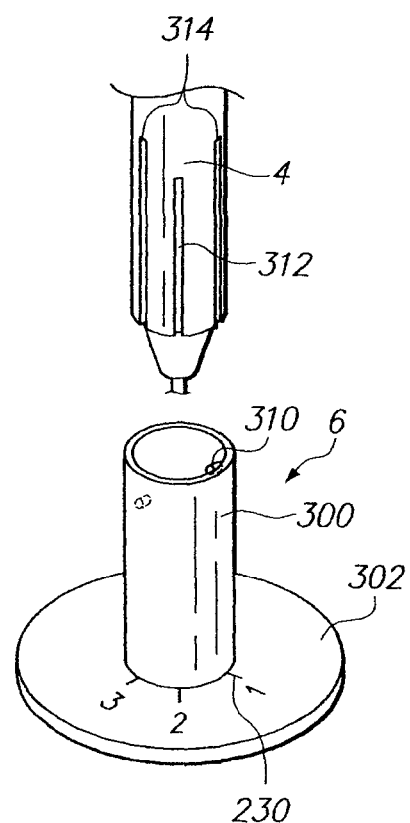
FIG. 5 is a perspective view of an indexing device in accordance with other embodiments.

FIG. 5 illustrates a variation of the indexing device 6 in accordance with other embodiments. The indexing device 6 also includes a tubular portion 300 and a base portion 302. However, unlike the embodiments of FIG. 4, the indexing device 6 does not have a plurality of slots in the wall of the tubular portion 300. Instead, the indexing device 6 has a plurality of extensions 310 secured to the tubular portion 300. In such cases, the treatment device 4 has a recess 312 sized to mate with each of the extensions 310, thereby controlling a position of the treatment device 4 relative to the tubular portion 300. The treatment device 4 also includes additional recesses 314 for accommodating the rest of the extensions 310 while the recess 312 is engaged with one of the extensions 310. During use, the treatment device 4 is placed into the tubular portion 300 such that the recess 312 mates with one of the extensions 310. The position of each of the extensions 310 at the tubular portion 300 determines how far the treatment device 4 can translate relative to the tubular portion 200, thereby ensuring that the treatment device 4 will be predictably placed at a desired position. If desired, during treatment, the treatment device 4 can be retracted proximally relative to the tubular portion 300, and reinserted into the tubular portion 300 such that the recess 312 mates with another of the extensions 310, thereby predictably placing the treatment device 4 at a second desired position.

It should be noted that the configuration of the indexing device 6 should not be limited by the examples discussed previously, and that the indexing device 6 can have other configurations in other embodiments.

Figure 6A:
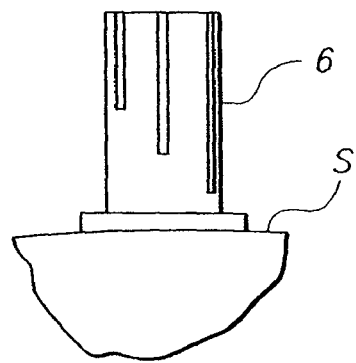
FIGS. 6A-6F illustrate a method for treating tissue in accordance with some embodiments.
Figure 6B:
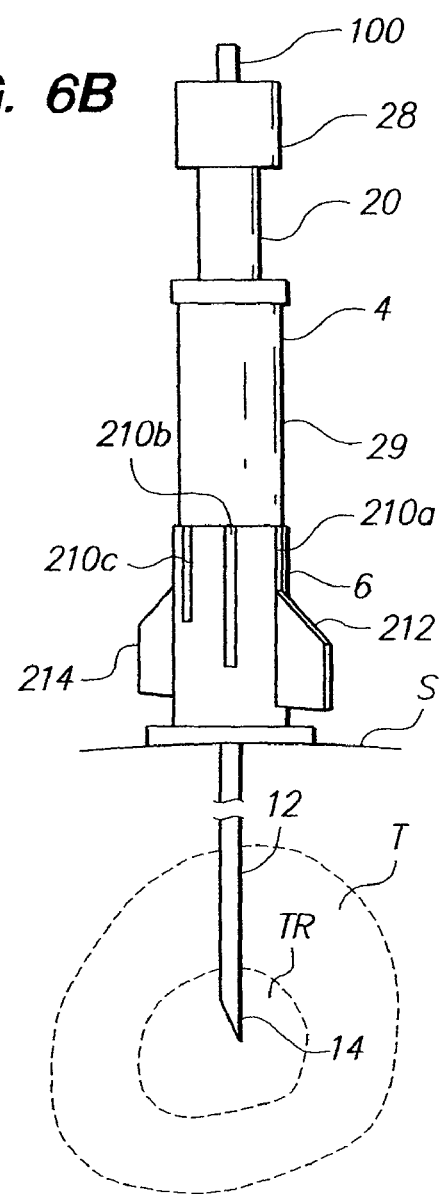

Referring now to FIGS. 6A-6F, the operation of the tissue treatment system 2 is described in treating a treatment region TR within tissue T located beneath the skin or an organ surface S of a patient. First, the indexing device 6 is placed against a patient's surface S (FIG. 6A). The cannula 12 is then inserted into the tubular portion 200 of the indexing device 6, and is advanced until the extensions 212, 214 of the treatment device 4 engage with a first group of opposing slots (one of them being slot 210a) at the tubular portion 200. The cannula 12 may have a sharpened tip, e.g., in the form of a needle, to facilitate introduction to the tissue T. It is also desirable that the cannula 12 be sufficiently rigid, i.e., have a sufficient column strength, so that it can be accurately advanced through tissue T without significant bending or buckling. In the illustrated embodiments, the engaged slots 210 are the deepest slots, which allows the distal end 14 of the cannula 12 to be introduced within the treatment region TR, and be placed at the distal end of the treatment region TR (FIG. 6B).

Figure 6C:
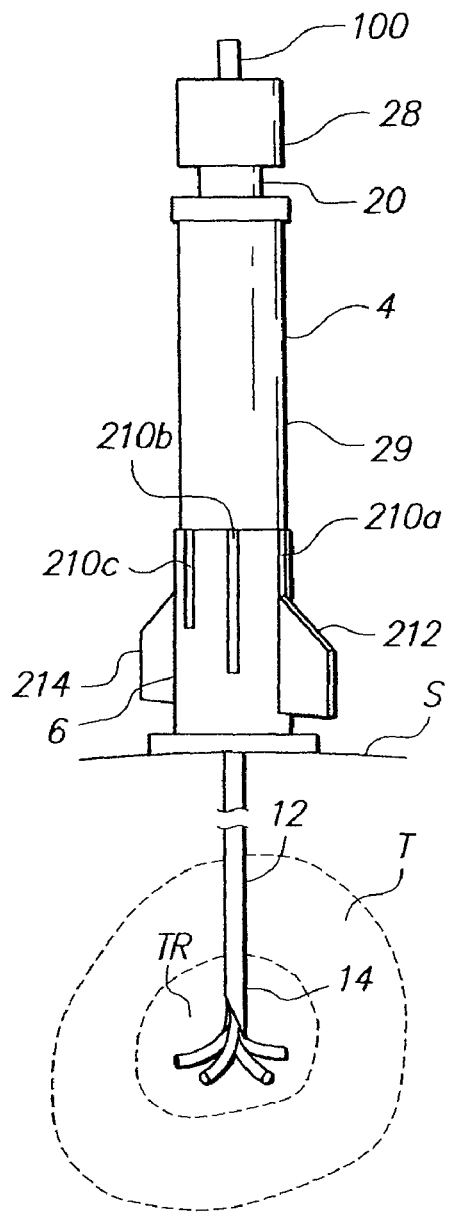

Next, the shaft 20 is advanced distally relative to the cannula 12 to deploy the delivery tubes 26 radially outward from the distal end 14 of the cannula 12 (FIG. 6C). Particularly, the shaft 20 is advanced sufficiently, so that the array 30 of delivery tubes 26 is fully deployed to span at least a portion of the treatment region TR. Alternatively, the delivery tubes 26 may be partially deployed or deployed incrementally in stages during a procedure (thereby allowing particles be delivered at different radial positions relative to a longitudinal axis of the treatment device 4).

Figure 6D:
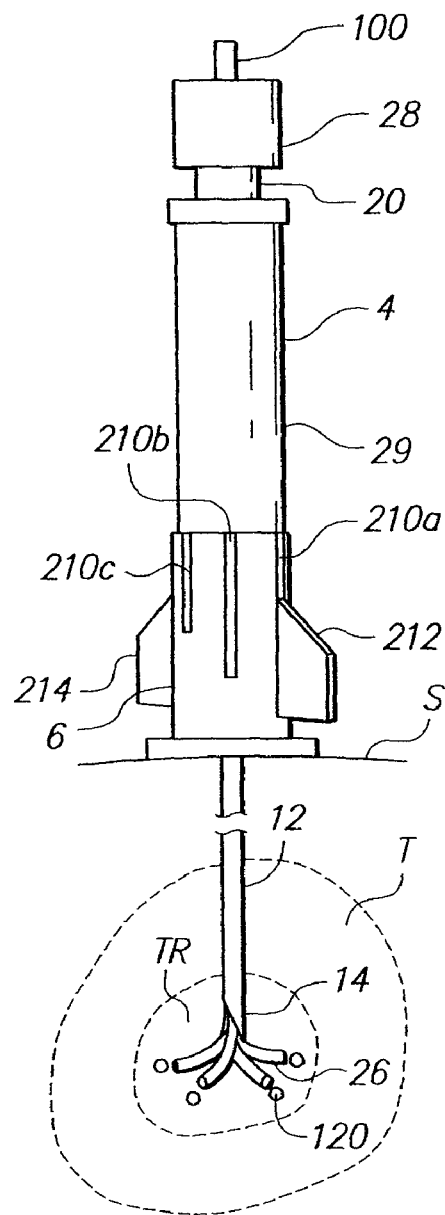

After the delivery tubes 26 are deployed, the plunger assembly 100 is advanced distally relative to the shaft 20 to deploy a treatment particle 120 from each of the delivery tubes 26 (FIG. 6D). As illustrated in the figure, the indexing device 6 allows the treatment particles 120 be delivered to a first portion of the treatment region TR in a predictable manner.

Figure 6E:
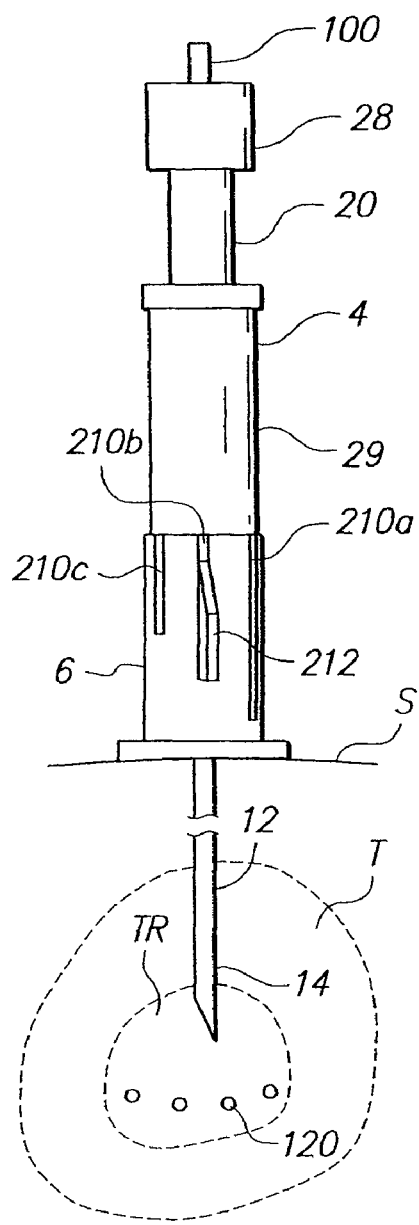
Figure 6F:
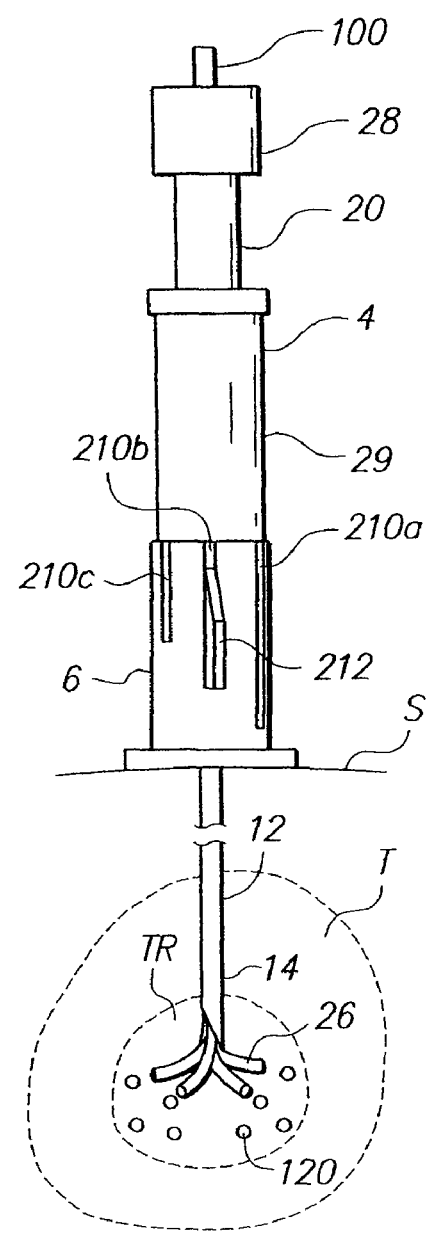

If it is desired to deliver additional treatment particles to other portion(s) of the treatment region TR, the shaft 20 can be retracted proximally relative to the cannula 12 to retract the delivery tubes 26. The cannula 12 is then retracted proximally until the extensions 212, 214 are disengaged from the first engaged slots of the indexing device 6. The cannula 12 is then turned axially and advanced relative to the indexing device 6 until the extensions 212, 214 engage with a second set of opposing slots of the indexing device 6 (FIG. 6E). As shown in the figure, because the second slot 210b is shorter than the first slot 210a, the distal end 14 of the cannula 12 is proximal to the first group of delivered treatment particles 120. Next, the shaft 20 is advanced distally relative to the cannula 12 to deploy the delivery tubes 26 radially outward from the distal end 14 of the cannula 12, and the plunger assembly 100 is advanced distally to deploy a second group of treatment particles 120 at a second portion of the target region TR (FIG. 6F).

If desired, the above steps of retracting the delivery tubes 26, retracting the cannula 12, reinserting the cannula 12, redeploying the delivery tubes 26, and advancing the plunger assembly 100, can be repeated until a sufficient number of treatment particles 120 have been delivered to cover the treatment region TR.

As can be appreciated by those skilled in the art, the indexing device 6 and the uniformly spaced delivery tubes 26 allow the treatment particles to be delivered to the treatment region TR in an uniform and/or predictable manner. The treatment system 2 is easy to use, and requires little technique by the physician. Also, use of the treatment device 4 to deliver treatment particles 120 directly to the target site (i.e., without using a vessel to distribute the particles) reduces the risk that the treatment particles 120 will migrate to an unintended site.

Although the above embodiments have been described with reference to treatment devices configured for delivering treatment particles, the scope of the present invention should not be so limited. In other embodiments, the treatment device 4 can be other types of medical devices, or components of other types of medical devices. For examples, in other embodiments, the treatment device 4 can be a conventional needle or a surgical cutting device. In such cases, the indexing device 6 can still be used to control the position of the treatment device 4 relative to a target tissue region.

In further embodiments, the treatment device 4 can be an ablation device having one or more electrodes. For example, the treatment device 4 can be an ablation apparatus that includes a plurality of electrode tines deployable from a cannula, such as those described in U.S. Pat. No. 5,855,576. Each of the tines includes a proximal end that is coupled to a generator, and a distal end that may project from a distal end of the cannula. The tines are arranged in an array with the distal ends located generally radially and uniformly spaced apart from the distal end of the cannula. The tines may be energized in a bipolar mode (i.e., current flows between closely spaced electrode tines) or a monopolar mode (i.e., current flows between one or more electrode tines and a larger, remotely located common electrode) to heat and necrose tissue within a precisely defined volumetric region of target tissue. When using the above described devices in percutaneous interventions, the cannula is inserted into the indexing device 6 and through a patient's skin. When the distal end of the cannula is desirably positioned, the tines are then deployed out of the distal end of the cannula to penetrate target tissue, and are energized to ablate the target tissue. The indexing device 6 can then be used to control a position of the distal end of the cannula relative to a target site, thereby allowing multiple ablation zones be created at desired positions. For example, a first ablation zone can be created at a first region of a target region, and the indexing device 6 can be used to create a second ablation zone at a second region that is proximal to the first region. The second ablation zone may or may not overlap a portion of the fist ablation zone. As will be appreciated by those skilled in the art, the longitudinal indexing feature provided by the indexing device 6 allows a physician to create ablation zones in a predictable and repeatable manner.

Although particular embodiments have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A tissue treatment system comprising:
   an elongated treatment device having a proximal end a distal end and a lumen extending there between, the elongated treatment device comprising at least one extension projecting therefrom;
   a shaft slidably disposed with the lumen of the elongated treatment device, the shaft including a plurality of delivery tubes carried by a distal portion of the shaft, the delivery tubes including respective lumens configured for carrying a treatment material;
   a plunger assembly slidably disposed relative to the shaft and configured to push the treatment material out of the respective lumens of the delivery tubes; and
   an indexing device comprising a receiving portion having a plurality of slots configured to receive the at least one extension, at least some of the plurality of slots having different lengths.

2. The system of claim 1, wherein a plurality of extensions project from the elongated treatment device.

3. The system of claim 2, wherein the plurality of extensions are located on opposing sides of the elongated treatment device and wherein the plurality of slots comprises a plurality of pairs of opposing slots disposed in the receiving portion, each respective opposing pair having substantially the same slot length.

4. The system of claim 1, wherein the elongated treatment device comprises a single extension and the plurality of slots comprise slots of different lengths.

5. The system of claim 1, wherein the treatment material comprises treatment particles.

6. The system of claim 1, wherein the treatment material comprises a liquid.

7. The system of claim 1, wherein the treatment material comprises a gel.

8. The system of claim 5, wherein the treatment particles are radioactive.

9. The system of claim 5, wherein the treatment particles comprise a bioactive agent.

10. The system of claim 9, wherein the bioactive agent harms or destroys tissue.

11. The system of claim 1, wherein the delivery tubes have a cross-sectional shape selected from the group consisting of rectangular, circular, elliptical, and square.

12. The system of claim 1, further comprising a handle affixed to a proximal portion of the shaft.

13. The system of claim 1, wherein the indexing device comprising a base portion affixed to the receiving portion.

14. The system of claim 1, wherein the plunger assembly comprises a proximal portion and a plurality of distal portions, the plurality of distal portions configured to push the treatment material out of the respective lumens of the delivery tubes.

15. The system of claim 1, wherein the receiving portion has a circular cross-section.

16. A tissue treatment system comprising:
    an elongated treatment device having a proximal end a distal end and a lumen extending there between, the elongated treatment device comprising a plurality of slots, at least some of the plurality of slots having different lengths;
    a shaft slidably disposed with the lumen of the elongated treatment device, the shaft including a plurality of delivery tubes carried by a distal portion of the shaft, the delivery tubes including respective lumens configured for carrying a treatment material;
    a plunger assembly slidably disposed relative to the shaft and configured to push the treatment material out of the respective lumens of the delivery tubes; and
    an indexing device comprising a receiving portion having at least one extension projecting from the receiving portion and configured to engage with the plurality of slots in the handle body.

17. The system of claim 16, wherein the receiving portion has a plurality of extensions projecting there from.

18. The system of claim 17, wherein the plurality of extensions are located on opposing sides of the receiving portion and wherein the plurality of slots comprises a plurality of pairs of opposing slots disposed in the elongated treatment device, each respective opposing pair having substantially the same slot length.

19. The system of claim 16, wherein the receiving portion comprises a single extension and the plurality of slots comprise slots of different lengths.

20. The system of claim 16, wherein the treatment material comprises treatment particles.

21. The system of claim 16, wherein the treatment material comprises a liquid.

22. The system of claim 16, wherein the treatment material comprises a gel.

23. The system of claim 20, wherein the treatment particles are radioactive.

24. The system of claim 20, wherein the treatment particles comprise a bioactive agent.

25. The system of claim 24, wherein the bioactive agent harms or destroys tissue.

26. The system of claim 16, wherein the delivery tubes have a cross-sectional shape selected from the group consisting of rectangular, circular, elliptical, and square.

27. The system of claim 16, further comprising a handle affixed to a proximal portion of the shaft.

28. The system of claim 16, wherein the indexing device comprising a base portion affixed to the receiving portion.

29. The system of claim 16, wherein the plunger assembly comprises a proximal portion and a plurality of distal portions, the plurality of distal portions configured to push the treatment material out of the respective lumens of the delivery tubes.

30. The system of claim 16, wherein the receiving portion has a circular cross-section.

31. A method for treating tissue, comprising:
    placing an indexing device against a surface of a body, the indexing device comprising at least one extension projecting from the indexing device;
    inserting a treatment device into the indexing device, the treatment device including a plurality of slots, at least some of the plurality of slots having different lengths;
    deploying a plurality of delivery tubes from the treatment device such that the plurality of delivery tubes are at a first position within a target tissue region; and
    delivering a treatment material from the plurality of delivery tubes to the target tissue region.

32. The method of claim 31, wherein the treatment material comprises treatment particles.

33. The method of claim 31, wherein the treatment material comprises a liquid.

34. The method of claim 31, wherein the treatment material comprises a gel.

35. The method of claim 32, wherein the treatment particles are radioactive.

36. The method of claim 32, wherein the treatment particles comprise a bioactive agent.

\* \* \* \* \*